United States Patent [19]

Sredni et al.

[11] Patent Number: 5,126,149
[45] Date of Patent: Jun. 30, 1992

[54] METHOD OF INDUCING THE PRODUCTION OF CYTOKINES

[75] Inventors: Benjamin Sredni, Beni Brak; Michael Albeck, Ramat-Gan, both of Israel

[73] Assignee: Bar-Ilan University, Ramat-Gan, Israel

[21] Appl. No.: 302,002

[22] Filed: Jan. 26, 1989

[51] Int. Cl.⁵ .................. A01N 59/16; A61K 33/24
[52] U.S. Cl. ............................ 424/650; 514/12; 514/49; 514/50; 514/716; 514/885
[58] Field of Search ............. 424/650; 514/12, 49, 514/50, 75, 716, 885

[56] References Cited
PUBLICATIONS

Chemical Abstracts 95:78830b (1981).

Primary Examiner—Nathan M. Nutter
Attorney, Agent, or Firm—Hedman, Gibson & Costigan

[57] ABSTRACT

The present invention provides a method for the stimulation of the production of lymphokines which comprises the administration of an effective amount of a tellurium tetrahalide.

15 Claims, No Drawings

METHOD OF INDUCING THE PRODUCTION OF CYTOKINES

BACKGROUND OF THE INVENTION

This invention provides novel compositions and methods for the inducement of cytokines production in humans.

In U.S. Pat. No. 4,761,490, the applicants disclosed that certain tellurium derivatives will induce the production of cytokines such as lymphokines.

The known types of lymphokines include, in addition to Interleukin-2 (IL-2), B-cell factors, Macrophage activation factor (MAF), Interleukin-3 (IL-3), Colony Stimulating Factor (CSF), Tumor Necrosis Factor and other factors produced by monocytes such as Interleukin-1 (IL-1) and Gamma Interferon. All of these factors are elaborated by white blood cells and are collectively known as cytokines.

The present invention is based on the discovery that tetravalent tellurium halides are capable of stimulating the production of cytokines when they are administered to a human. This discovery makes possible a novel chemotherapeutic approach to the treatment of immune deficiencies, autoimmune diseases and infectious diseases using the tetravalent tellurium halides as adjuvants or as primary therapeutic agents.

Accordingly, it is an object of this invention to provide a novel method for producing in vitro cytokines such as lymphokines.

It is also an object of this invention to provide a novel method for producing in vivo cytokines such as lymphokines.

It is also an object of this invention to provide novel methods for the treatment of immune deficiencies, autoimmune disease and infectious diseases.

These and other objects of the invention will become apparent from a review of the specification.

SUMMARY OF THE INVENTION

The novel compositions of the invention comprise a tellurium tetravalent halide and a pharmaceutically acceptable carrier. The tetravalent tellurium tetrahalides include tellurium tetrachloride, tellurium tetrabromide, tellurium tetraiodide and tellurium tetrafluoride.

The compositions of the invention may be administered to mammals for treatment of immune deficiencies, autoimmune diseases and infectious diseases using amounts of the composition that are effective in each condition. The treatment will alleviate the symptoms of these diseases by causing the mammalian body to produce increased amounts of lymphokines. The invention also contemplates the in vitro production of increased amounts of cytokines such as lymphokines and or their receptors and the use of these materials as therapeutic agents to be administered to mammals for the alleviation of cancer, immune deficiencies and infectious diseases. It is contemplated that the composition of the invention may be administered in combination with other anti-cancer chemotherapeutic agents such as AZT cyclophosphamide, methotrexate, interferon, 5-fluorouracil and the like.

The term is used to include leukemia and solid tumors that arise spontaneously or in response to a carcinogenic agent, by irradiation or by oncoviruses. These conditions are well known to those who are skilled in the art and include such conditions as adrenal tumors, bone tumors, gastrointestinal tumors, brain tumors, skin tumors, lung tumors, ovarian tumors, genitourinary tumors and the like. The Merck Manual 13th Edition, Merck & Co. (1977) describes many of these conditions. Pages 647-650; 828-831; 917-920; 966; 970-974; 1273; 1277; 1371-1376; 1436-1441; 1563; 1612-1615 of that publication are incorporated herein by reference.

The term immunodeficiency diseases is used to describe a diverse group of conditions such as Acquired Immunodeficiency Syndrome (AIDS) characterized chiefly by an increased susceptibility to various infections with consequent severe acute, recurrent and chronic disease which result from one or more defects in the specific or nonspecific immune systems. Pages 205-2330 of the Merck Manual 13th Edition describe these conditions and they are incorporated herein by reference.

The term autoimmune diseases includes disorders in which the immune system produces autoantibodies to an endogenous antigen, with consequent injury to tissues. Pages 241-243 of the Merck Manual 13th Edition describe these conditions and they are incorporated herein by reference.

The term infectious diseases includes those pathologic conditions that arise from bacterial, viral or fungus organisms that invade and disrupt the normal function of the mammalian body. Pages 3-147 of the Merck Manual 13th Edition describe these conditions and they are incorporated herein by reference.

The compositions may be administered orally, parenterally, transcutaneously, topically or by contacting mucous membranes. The compositions may be administered orally with or without a carrier although if oral administration is employed, the composition may be administered in capsules or tablets using conventional excipients, binders, disintegrating agents and the like. The parenteral route is presently preferred and compositions may be prepared by dissolving the compound in a suitable solvent such as water, aqueous buffer, glycerol or PBS. The parenteral route may include the intramuscular, intravenous, intradermal using a sustained release carrier and subcutaneous route. The concentration of the compositions in the pharmaceutical carrier is not critical and is a matter of choice. Remingtons Practice of Pharmacy, 9th, 10th and 11th Ed. describe various pharmaceutical carriers and is incorporated herein by reference.

It is believed that the tellurium tetrahalides will decompose in water to form various tellurium derivatives. For this reason when solutions employed, it is preferred to use freshly prepared solutions although solutions which are not freshly prepared will be biologically active.

The dosage of the compositions used to stimulate lymphokine production or treat a specific disease condition described herein may be varied depending on the particular disease and the stage of the disease. Generally, an amount of the compound may be administered which will range from $0.01 \times 10^{-3}$ to $1 \times 10^{-3}$ g/Kg of body weight and preferably from $0.02 \times 10^{-3}$ to $0.5 \times 10^{-3}$ g/Kg of body weight. For example a dosage of about 2-8 mg. preferably every other day for a 75 Kg. mammal is contemplated as a sufficient amount to induce the production of lymphokines but the dosage may be adjusted according to the individual response and the particular condition that is being treated. For the treatment of AIDS about 1.0-9.0 mg/m$^2$ may be given three times a week. In addition, the compound may be given concomitantly with other anti-AIDS agents such as 9-(1,3-dihydroxy-2-propoxymethyl) guanine (DHPG); and/or AZT. These agents may be administered at conventional dosages which are known to those who are skilled in the art.

In addition to the treatment of the mammalian disorders described hereinabove, the compounds may be utilized for veterinary purposes in the treatment of viral and immune diseases that afflict horses, ungulates and fowl as well as other species. These disorders may be treated using the dosages set forth hereinabove for the treatment of mammalian disorders.

For in vitro use, cells may be stimulated to produce lymphokines by use of $1 \times 10^{-8}$ to $1 \times 10^{-4}$, preferably $1 \times 10^{-7}$ to $1 \times 10^{-5}$ g of compound per about $10^6$ cell/ml. Plant bacterial infectious such as crown gall may be treated by the application of a solution containing an effective amount of the composition of the invention, preferably containing about 0.1% of the active component.

DESCRIPTION OF THE PREFERRED EMBODIMENTS

The following examples are given to illustrate the invention and it is understood that it does not limit the scope of the invention.

EXAMPLE 1

The compound tellurium tetrachloride was tested for its effect on the proliferation of splenocytes in vitro. Spleen cells were obtained from male Balb-C mice 6-8 weeks of age. The spleens were removed and the spleen cells were pushed through stainless steel 60 mesh nets (United States standard) resting in 5 mm Petri dishes containing PBS in order to separate the cells. The cells were then collected into centrifuge tubes and spun at 1000 rpm for 10 minutes. The supernatant was discarded and cells were treated with 5 ml of hypotonic buffer (0.15M $NH_4Cl$; 0.01M $KHCO_3$ dissolved in double distilled water, pH 7.2) for exactly two minutes. Thereafter, PBS was added to the cells and the test tubes were centrifuged for 10 minutes at 1000 rpm. The cells were rinsed twice and counted in a heamocytometer using trytan blue to test for viability. The cells were brought to a concentration of $10^6$ viable cells/ml using enriched RPMI with 10% fetal calf serum. The cells were placed in a 96 well culture plate (0.1 ml cells) containing the stated amounts of tellurium tetrachloride and Control to which was added 20 ng/ml PMA (Phorbol Myristic Acetate). The cells were incubated for 48 hours, labelled for an additional 24 hours with 1 u Ci/well of $^3H$-thymidine and harvested. The results are set forth in Table I.

TABLE 1

| µg/ml | TeCl$_4$ | Control* |
|---|---|---|
|  | CPM |  |
| 5 | 1,093 | 292 |
| 2.5 | 267 | 327 |
| 1.25 | 280 | 1,457 |
| 0.6 | 447 | 4,187 |
| 0.3 | 5,597 | 56,195 |
| 0.1 | 73,475 | 66,455 |
| 0.07 | 45,342 | 38,142 |
| 0.03 | — | 13,573 |
| PMA alone - 18,796 |  | PBS alone - 1800 |

*ammonium trichloro(dioxoethylene-0,0')tellurate

These results show that TeCl$_4$ is capable of inducing the proliferation of mouse spleen cells in vitro.

EXAMPLE 2

Tellurium tetrachloride was tested for its effect on proliferation of human MNC in vitro. MNC were obtained by layering buffy coats from normal human donors on a Ficoll-Hypaque gradient. Cells were rinsed, brought to a concentration of $10^6$ cells/ml, divided into wells of a 96 well culture plate and incubated for 72 hours with varying concentrations of TeCl$_4$ or Control. Plates were labelled for an additional 24 hours with $^3$-H-thymidine and harvested. The results are set forth in Table II.

TABLE II

| µg/ml | TeCl$_4$ | Control* |
|---|---|---|
|  | CPM |  |
| 2.5 | 1,027 | 275 |
| 1 | — | 5,027 |
| 0.7 | 6,883 | 6,407 |
| 0.3 | 8,762 | 8,413 |
| 0.1 | 9,383 | 13,952 |
| 0.07 | 3,843 | 3,300 |
| 0.03 | 2,779 | 2,943 |
| PMA alone - 1,020 |  |  |

*ammonium trichloro(dioxoethyle-0,0')tellurate

These results show that TeCl$_4$ can stimulate human MNC to proliferate in vitro.

EXAMPLE 3

Tellurium Tetrachloride (TeCl$_4$) and Control were tested for their effect on IL-2 production from mouse spleen cells in vitro. Spleen cells were obtained as described in Example 1. The cells were brought to a concentration of $5 \times 10^6$/ml using enriched RPMI with 10% fetal calf serum. Cells were placed in a 24 well culture plate containing the stated amount of tellurium tetrachloride or the Control, to which was added 20 ng/ml PMA (Phorbol Myristic Acetate). Cultures were incubated for 24 hours at 37° C. Supernatants were collected and tested for IL-2 content. The results are presented in Table IIIa (50% Supernatant) and Table IIIb (25% Supernatant).

TABLE IIIa

| (50% Supernatant) | | |
|---|---|---|
| µg/ml | TeCl$_4$ | Control* |
|  | CPM |  |
| 5 | 160 | 6,115 |
| 1 | 743 | 6,125 |
| 0.5 | 19,746 | 43,053 |
| 0.1 | 49,995 | 13,413 |
| PMA alone - 4,993 |  | PBS alone - 1,200 |

TABLE IIIb

| (25% Supernatant) | | |
|---|---|---|
| µg/ml | TeCl$_4$ | Control* |
|  | CPM |  |
| 5 | 1,229 | 2,902 |
| 1 | 4,273 | 24,912 |
| 0.5 | 16,422 | 51,567 |
| 0.1 | 27,680 | 28,877 |
| PMA alone - 4,993 |  | PBS alone - 1,200 |

*ammonium trichloro(dioxoethylene-0,0')-tellurate

These results show that TeCl$_4$ is capable of inducing the production of IL-2 in vitro.

| PBS contains | |
|---|---|
| NaCl | 8.0 g |
| KCl | 200 mg |
| Na$_2$HPO$_4$ | 1150 mg |
| KH$_2$PO$_4$ | 200 mg |
| CaCl$_2$ (anhyd.) | 100 mg |
| Mg Cl$_2$6H$_2$O | 100 mg/L |
| H$_2$O | sufficient to make 1 liter |

We claim:

1. A pharmaceutical composition which comprises an amount of tellurium tetrahalide which is effective for inducing production of cytokines in a mammal and a pharmaceutically acceptable carrier.

2. A pharmaceutical composition as defined in claim 1 which comprises a dosage unit consisting essentially of an amount of a tellurium tetrahalide which is effective for inducing the production of cytokines in a mammal and a pharmaceutically acceptable carrier.

3. A pharmaceutical composition as defined in claims 1 or 2 wherein the tellurium tetrahalide is tellurium tetrachloride.

4. A pharmaceutical composition as defined in claims 1 or 2 wherein the tellurium tetrahalide is tellurium tetrabromide.

5. A pharmaceutical composition as defined in claims 1 or 2 wherein the tellurium tetrahalide is tellurium tetrafluoride.

6. A pharmaceutical composition as defined in claims 1 or 2 wherein the tellurium tetrahalide is tellurium tetraiodide.

7. A method of stimulating the production of lymphokines which comprises administering to a host an effective amount of a tellurium tetrahalide for inducing the production of cytokines in a host.

8. A method of stimulating the production of lymphokines as defined in claim 7 wherein the tellurium tetrahalide is tellurium tetrachloride.

9. A method of stimulating the production of lymphokines as defined in claim 7 wherein the tellurium tetrahalide is tellurium tetraiodide.

10. A method of stimulating the production of lymphokines as defined in claim 7 wherein the tellurium tetrahalide is tellurium tetrabromide.

11. A method of stimulating the production of lymphokines as defined in claim 7 wherein the tellurium tetrahalide is tellurium tetrafluoride.

12. A method of stimulating the production of lymphokines as defined in claim 7 wherein the tellurium tetrahalide is tellurium tetraiodide.

13. A method as defined in claim 7 wherein the tellurium tetrahalide is administered for the treatment of AIDS alone or in combination with an amount of an anti-AIDS drug which is effective against AIDS.

14. A method of stimulating the production of lymphokines which comprises administering to a host an effective amount of tellurium tetrachloride for inducing the production of lymphokines in a host for the treatment of AIDS in combination with the anti-AIDS drug AZT.

15. A method as defined in claim 13 wherein the anti-AIDS drug is selected from the group consisting of cyclophosphamide, methotrexate, interferon and 5-fluorouracil.

* * * * *